United States Patent [19]

Flora et al.

[11] Patent Number: 4,710,710
[45] Date of Patent: Dec. 1, 1987

[54] SCANNING APPARATUS AND METHOD FOR INSPECTION OF HEADER TUBE HOLES

[75] Inventors: John H. Flora, Lynchburg; Robert E. Womack, Forest; Carlton E. Stinnett; Claude W. Dalton, both of Lynchburg, all of Va.

[73] Assignee: The Babcock & Wilcox Company, New Orleans, La.

[21] Appl. No.: 855,100

[22] Filed: Apr. 22, 1986

[51] Int. Cl.$^4$ ............... G01N 27/82; G01R 33/12
[52] U.S. Cl. ................. 324/220; 73/866.5; 165/11.2; 414/749
[58] Field of Search ............... 324/219–221, 324/262; 73/622, 623, 866.5; 33/178 F, 542–544; 414/590, 749; 228/103; 376/245, 249, 254; 165/11.2

[56] References Cited

U.S. PATENT DOCUMENTS 3,718,855  2/1973  Rogel et al. ............ 324/219 UX
3,831,084  8/1974  Scalese et al. ......... 324/219 X
4,142,154  2/1979  Couchman ............. 324/219
4,231,419  11/1980  Gugel ................. 165/11.2

FOREIGN PATENT DOCUMENTS 0060805  5/1980  Japan ................. 324/220

Primary Examiner—Gerard R. Strecker
Attorney, Agent, or Firm—Vytas R. Matas; Robert J. Edwards

[57] ABSTRACT

An apparatus for scanning header tube holes includes a probe assembly designed to engage the surface of the header encircling a header tube hole. The probe assembly includes a spring mounted sensor, in a preferred arrangement, an eddy current probe. A mechanism is provided for supporting and positioning the probe assembly. The mechanism is adapted, in operation, with resilient rings engaging the tube stub. A drive device is provided for imparting axial and circumferential movement to the probe relative to the surface of the hole which is to be inspected.

19 Claims, 5 Drawing Figures

SCANNING APPARATUS AND METHOD FOR INSPECTION OF HEADER TUBE HOLES

BACKGROUND OF THE INVENTION

The present invention relates to the inspection of header tube hole surfaces and, more particularly, to a new and improved scanning apparatus and method for inspecting surfaces of header tube holes.

Headers are used extensively in steam boilers as a means for joining fluid circuits and for distributing fluid to fluid circuits. Such headers typically comprise a large-diameter, heavy-walled cylindrical shell, circular in cross section, having multiple straight or bent tube stubs which extend partially into holes formed through the wall of the header. The tube stubs are fixed to the header via rolled tube joints or by welded tube connections. The end on the portion of each tube stub extending outside of the header is designed to be connected to a component of a fluid circuit, usually in the form of a tube which is welded to the tube stub.

Cracks that initiate from the header surface surrounding the tube holes in steam headers of boilers in fossil fuel burning electrical power plants can lead to failures which can cause costly unscheduled plant outages. If cracks are detected in early stages, however, plans can be made to repair or replace the header during scheduled maintenance and repair outages. Detection and characterization of cracks near the surface surrounding holes in structural components, by nondestructive testing, is often a key factor in assessing the condition and remaining useful life of a component. Crack characterization, i.e., measurement or estimates of depth, length and location of cracks that initiate from the surface of holes in headers is used with additional information to predict remaining life and to plan repair or replacement of the headers.

Cracks have been detected with boroscopes that use fiber optics technology. Access to the hole is obtained by cutting and removing a section of the tube or tube stub that leads into the header. The boroscope is manually inserted into the hole and rotated to inspect the entire circumference. However, proper focusing of the boroscope is difficult to achieve due to instrument sensitivity to changes in probe-to-surface distance. Therefore, quality and reliability of data is less than adequate without a mechanism which permits a controlled scan that maintains a relatively constant position and alignment of the probe. The same, as well as other difficulties, arise with regard to the use of other sensors including ultrasonic transducers and eddy current probes.

SUMMARY OF THE INVENTION

It is an object of this invention to provide a novel apparatus for supporting and positioning an inspection probe or the like within a header tube hole.

Another object of this invention is to provide means for examining successive portions of the surface of the header surrounding the header tube hole with an inspection probe or the like.

It is a still further object of this invention, to provide a method of inspecting header tube holes by performing rotary or axial scans, or both, to detect cracks and to calculate the depth of the cracks. An eddy current inspection technique is preferably utilized to obtain data for such calculations.

In accordance with a preferred embodiment of the apparatus of this invention, a probe is mounted to a tube stub mounting mechanism, connected to a drive which rotates and translates the probe within the header tube hole. The mounting mechanism is interconnected between the probe assembly and the drive. The mounting mechanism is designed to be detachably connected to the tube stub for supporting the inventive apparatus. The probe includes spring means for pressing a probe sensor into engagement with the surface of the header surrounding the header tube hole.

In a preferred embodiment, the tube mounting mechanism includes a central hollow cylinder connected to the spring means. The spring means, and hence the sensor, is moveable responsive to movement of the hollow cylinder. A flanged tube is slidably disposed on the hollow cylinder. The tube mounting mechanism further includes a pair of expansible rings on the tubes and means on the tube for expanding the rings into supporting engagement with the tube stub. The hollow cylinder may be constructed of a flexible material for scanning bent tube stubs. The drive includes means for rotating and axially translating the hollow cylinder and the sensor therewith.

The various features of novelty which characterize the invention are pointed out with particularity in the claims annexed to and forming part of this specification. For a better understanding of the invention, its operating advantages and specific objects attained by its use, reference should be had to the accompanying drawing and descriptive matter in which there is illustrated and described a preferred embodiment of the invention.

BRIEF DESCRIPTION OF THE DRAWINGS

In the accompanying drawings, forming a part of this specification, and in which reference numerals shown in the drawings designate like or corresponding parts throughout the same.

DETAILED DESCRIPTION

Figure 1:
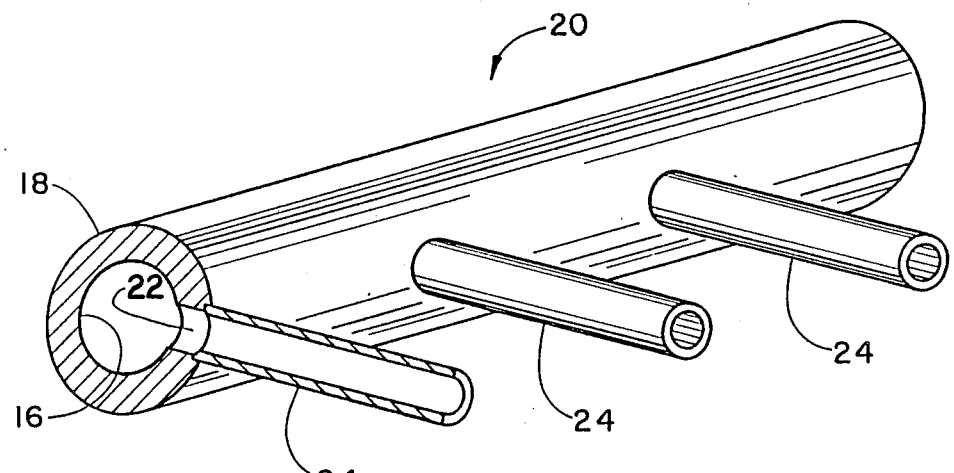
FIG. 1 is a perspective view, partly broken away, of a portion of a header.
Figure 2:
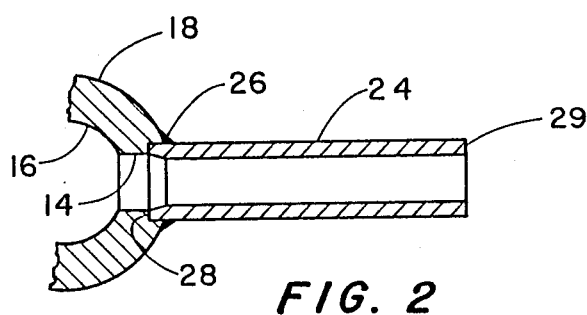
FIG. 2 is a partial sectional view of a header and a tube received within the header tube hole.

Referring now to the drawings in detail and in particular to FIG. 1, there is shown a cylindrical header 20 which has a plurality of holes 22 extending through the thickness of the header wall from the inner surface 16 to the outer surface 18 of the header 20. A plurality of tube stubs 24 are received within the holes 22 and are fixed to the header 20 by welding, as illustrated by welds 26 in FIG. 2. Alternatively, the tube stubs 24 may be fixed to the header by formation of a rolled joint. An end 28 of each tube stub 24 is located within the tube hole 22 at a position intermediate the inner and outer surfaces 16, 18 of the header 20 and distant from the inner surface 16 of the header 20.

The opposite ends 29 of each tube stub 24, which are located outside of the header 20, are designed to be connected to tubes (not shown) of an external fluid circuit to provide fluid communication between the header 20 and the fluid circuit for joining fluid streams passed to the header 20 or for distributing fluid streams passed from the header 20.

On occasion, it becomes necessary to disconnect the tubes of the fluid circuit from the tube stubs 24 and to inspect the peripheral surface 14 surrounding the header tube hole 22 and located intermediate the inner surface 16 and the end 28 of the tube stub 24 which is seated within the wall of the header 20.

Figure 3:
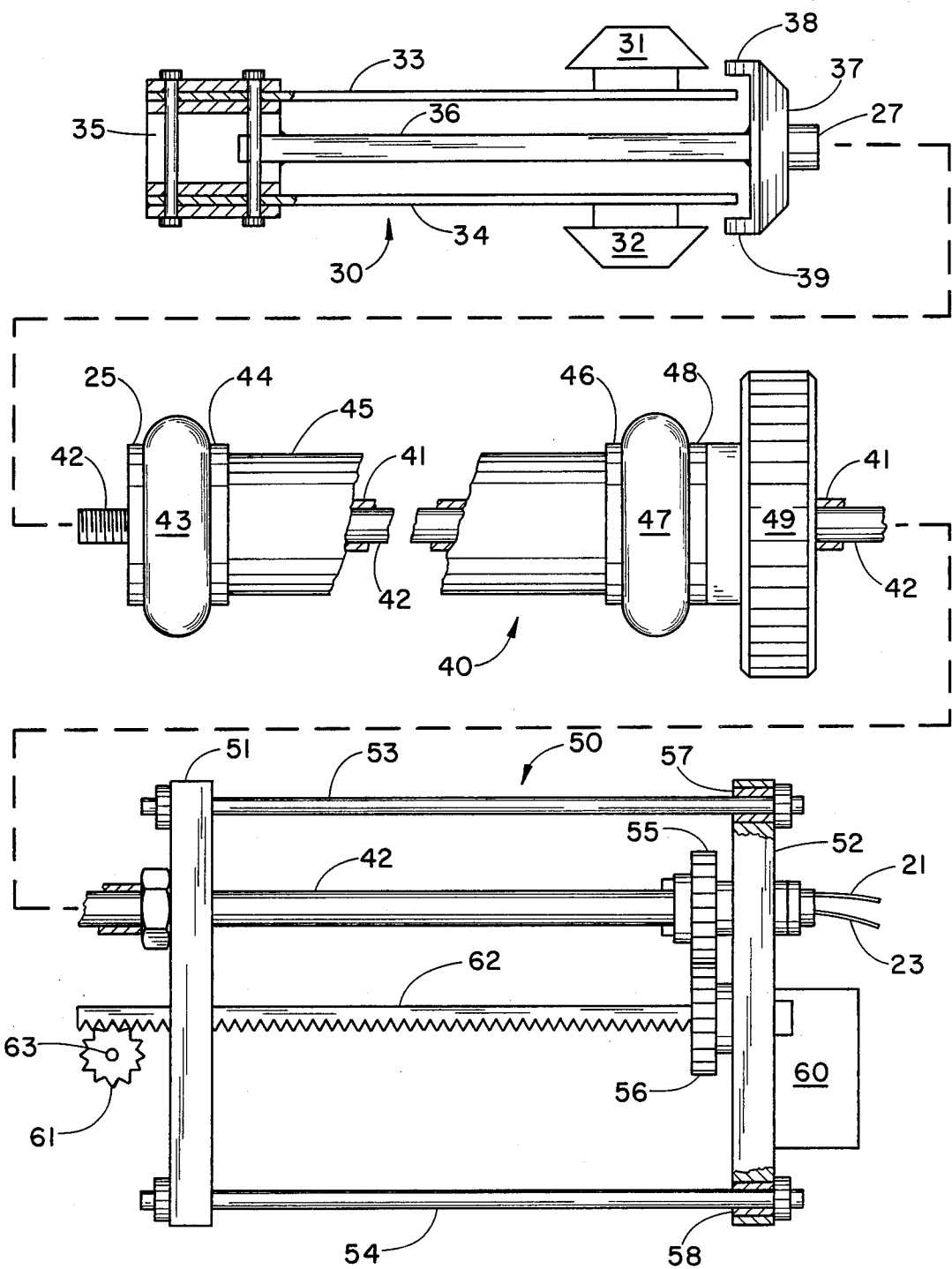
FIG. 3 is an exploded side view, partly in section, of a preferred embodiment of an apparatus according to the invention.

Referring to FIG. 3, an inspection apparatus, according to a preferred embodiment of the invention, includes a probe assembly 30 which is capable of being inserted through the tube stubs 24 of the header 20 and into the header tube holes 22. The probe assembly 30 is mounted to a tube stub mounting mechanism 40 which is designed to engage one of the tube stubs 24. Both the probe assembly 30 and the tube stub mounting mechanism 40 are connected to a drive carriage 50 which is operable to move the probe assembly 30 as is more particularly described hereafter.

The probe assembly 30 is provided with sensors 31, 32 supported for movement on one end of substantially parallel spring bars 33, 34, respectively. Each spring bar 33, 34 at its opposite end is secured, in cantilevered fashion, by a support plate, referred to herein as clamp block 35 composed of a number of plates which are bolted together. The clamp block 35, which is located at the leading end of the probe assembly 30, in turn, is mounted to an elongated support bar 36 which extends, away from the leading end of the probe assembly 30, between and substantially parallel to the spring bars 33, 34 and terminates beyond the spring bars 33, 34 in a C-shaped stop plate. The stop plate is composed of a crossbar 37 which extends substantially perpendicularly relative to the elongated axis of the support bar 36 and stop lugs 38, 39 at opposite ends of the crossbar 37 which overlap the ends of the respective spring bars 33, 34. An internally-threaded, tubular socket 27 is provided on the side of the stop plate opposite the support bar 36.

The tube stub mounting mechanism 40 is connected to the probe assembly 30, in the illustrated embodiment, by threaded engagement of the threaded end of a hollow cylinder 42 and the socket 27. As shown in FIG. 3, a flanged tube is mounted about the hollow cylinder 42. The hollow cylinder 42 may be moved freely relative to the flanged tube. The flanged tube has a flange 25 located at an end near the end of the hollow cylinder 42 which is coupled to the socket 27. Resilient locking rings or collars 43, 47, a sleeve 45, and spacer washers 44, 46, 48 are slidably received upon the tube 41 of the flanged tube intermediate the flange 25 of the flanged tube and an adjusting knob 49. The adjusting knob 49 is threadably engaged to the tube 41. The resilient locking collars 43, 47, in the preferred embodiment, have a diameter slightly larger than the sleeve 45, flange 25 and spacer washers 44, 46, 48 and is designed to approximate the internal diameter of the tube stubs 24.

The drive carriage 50 comprises a pair of generally parallel mounting plates 51, 52 with guide rods 53, 54 which extend parallel to each other.

The end of the flanged tube opposite the flange 25 is engaged to mounting plate 51 provided as part of the drive carriage 50. The hollow cylinder 42 freely passes through mounting plate 51 and is operatively mounted to mounting plate 52 in a manner more particularly described hereafter.

The hollow cylinder 42 is operatively attached to a gear 55 for rotation via a bearing mounted on the mounting plate 52. The gear 55 is connected to a rotational drive motor 60 or other means for imparting rotation to the hollow cylinder 42 via an intermediate gear 56.

Mounting plate 52 is slidably disposed on the guide rods 53, 54 and has a pair of bearings 57, 58 which are slidable along the guide rods 53, 54, respectively, to allow the mounting plate 52, with the hollow cylinder 42, gears 55, 56 and motor 60, to move rectilinearly and parallel to the guide rods 53, 54.

A pinion gear 61 drives a drive rack 62 to rectilinearly advance and retract the mounting plate 52. The drive rack 62 is connected to mounting plate 52 and freely extends through mounting plate 51. The pinion gear 61 is mounted on a drive shaft 63 which may be driven by suitable means, for example, a hand crank or stepping motor. In addition, a pair of pinion gears 61 may be provided on opposite sides of the carriage assembly, interconnected by drive shaft 63, for engagement with parallel drive racks.

Figure 4:
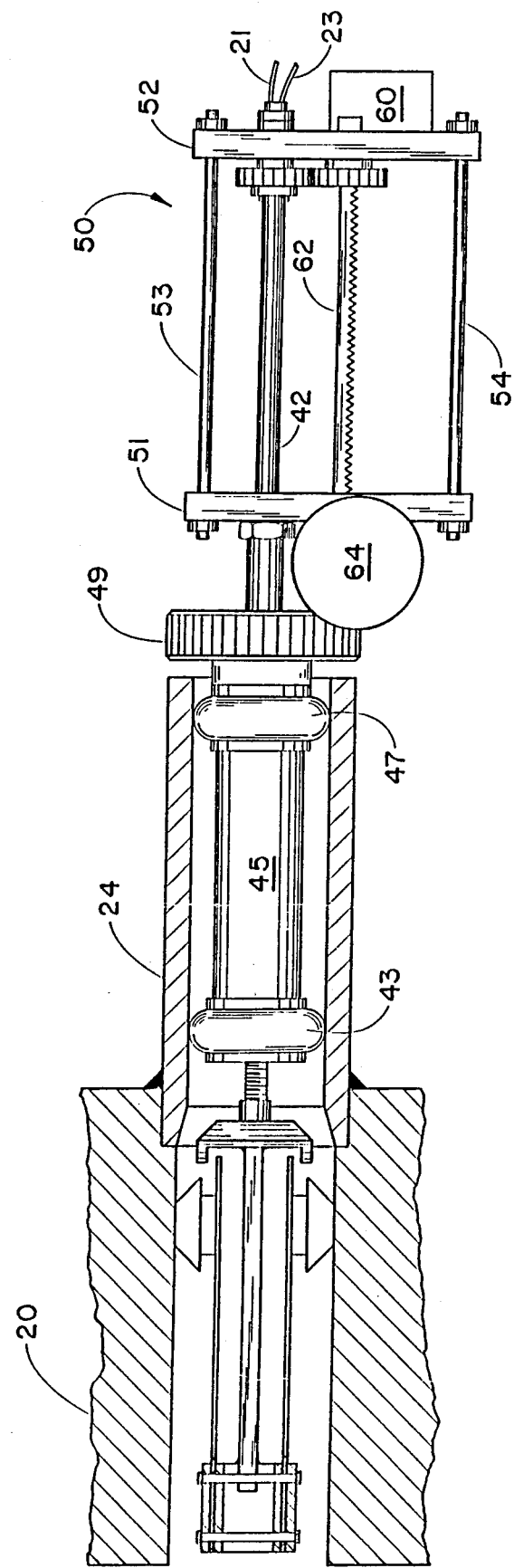
FIG. 4 is a schematic illustration of an apparatus of the type illustrated in FIG. 3 mounted in position within a header tube hole for inspecting the header hole in accordance with the invention.

FIG. 4 is a schematic representation showing the apparatus of the invention in position for inspecting the peripheral surface 14 of the header tube hole 22 of header 20.

In operation, the tube stub 24, which is seated within the hole 22 which is to be inspected, is disconnected from the fluid circuit to which it is normally attached. The probe assembly 30 is inserted through the tube stub 24 and into the hole 22 until the tube stub mounting mechanism 40 is positioned with the tube stub 24. As the probe assembly 30 passes through the tube stub 24, the spring bars 33, 34 which resiliently urge the sensors 31, 32 outwardly of the support bar 36 are compressed toward the support bar 36. On passing tube stub end 28, however, the spring bars 33, 34 expand outwardly to press the sensors 31, 32, against the peripheral surface 14. The outward movement of the spring bars is restricted by contact with the stop lugs 38, 39 of the C-shaped stop plate. The stop lugs 38, 39 restrict lateral movement of the spring bars 33, 34 beyond the inner diameter of the tube stub 24 so that the probe assembly can be retrieved from the header 20 without sustaining damage to the probe and sensors. The sensors 31, 32 in the preferred embodiment, comprise housings having tapered edges to further facilitate retrieval of the probe assembly 30.

The adjusting knob 49 is then tightened. The tightening of the adjusting knob 49 causes displacement of the sleeve 45, and spacer washers 44, 46, 48 toward the flange 25. This causes the resilient, expansible rings or locking collars 43, 47 to diametrically expand into supporting engagement with the tube stub 24. The circumferential contact of resilient locking collars which may, for example, be rubber rings, with the tube stub 24, facilitates support and reference for the apparatus.

As illustrated in FIGS. 3 and 4, the hollow cylinder 42 comprises a rigid tubular member composed, for example, of type 304 stainless steel.

In an alternate embodiment, the hollow cylinder 42 may be a flexible tubular member, for example, a braided steel tube. Braided steel flexible tubes are typically flexible to bending but extremely rigid to torsional forces. Utilization of a flexible hollow cylinder will permit the probe to be inserted through bent tube stubs.

Figure 5:
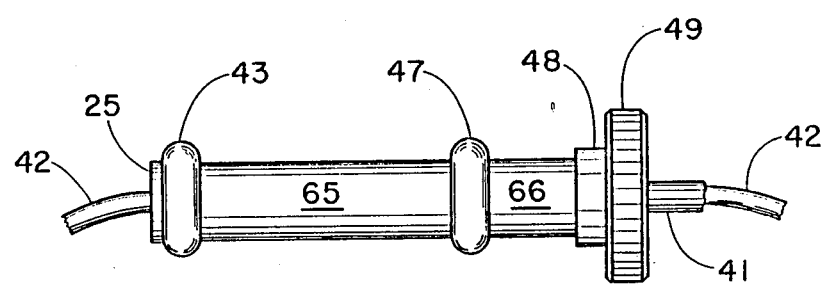
FIG. 5 is a view of the tube stub mounting mechanism in accordance with another embodiment of the invention.

In such case, the tube stub mounting mechanism can be modified, as shown in FIG. 5, to omit the central spacer washers, and alternatively to include two short sleeves 65, 66.

The electrical connections to the probe, e.g., electrical lines 21, 23, are contained within the hollow cylinder 42. The gears 55, 56 mounted at the end of the cylinder 42, link the probe assembly 30 to the rotational drive motor 60. The cylinder 42 rotates in the bearing 59 within the mounting plate 52. A second motor 64, illustrated in FIG. 4, is operable to drive the pinion gear 61 and drive rack 62 to slide the mounting plate 52 along the guide rods 53, 54 so that the probe assembly 30 moves in the axial direction of the header tube hole. The pinion gear 61 is preferably mounted to the mounting plate 51. Control can be provided for both motors 60, 64 for a coordinated sequence of rotational probe scans at various axial positions along the length of the header tube hole. When stepping motors are used, relatively precise rotational and axial positioning of the probe assembly sensors 31, 32 can be obained.

Although two springs 33, 34, as illustrated in FIG. 4, are provided to support two support sensors 31, 32, there are many applications where only one sensor is needed. In such case, a housing fixture that does not contain a sensor is fastened to one spring, to provide a counter force to balance the other sensor spring. This counter force helps keep the probe assembly 30 near the central axis of the hole. The forces of the leaf springs tend to move the sensor into engagement with the surface of the hole. The sensor housing can be mounted on sponge rubber pads to assist in alignment of the sensors. The flat spring and sensor backing, in such case, provide sufficient surface area for application of an adhesive bond to secure the sponge rubber pad.

The apparatus of the invention provides a systematic controlled means for scanning one or more transducers, or other inspection devices, over the surface of a header tube hole. It allows good transducer alignment with relatively constant probe-to-tube surface distance throughout the scan. Moreover, the use of electronically controlled stepping motors provides precise rotational and axial positioning of the sensors. The use of separate motors for sensor rotation and axial movement offers particular versatility in scanning the surface of the header hole. Rotational scanning can be executed without slip rings and without twisting the sensor cables. This can be accomplished by programming the stepping motor control to return to starting position before repeating the scan at a new axial location. Stepping motors, moreover, can be associated with digital control to facilitate data acquisition at predesignated locations for repeated scans. This provides spacially coherent signal responses which are the basis for improved accuracy in the interpretation of sensor data.

The device of the invention comprises a simple design which can be embodied in a light weight structure for ease of use. The expandable rubber rings hold the device in place throughout the inspection. Finally, the stop lugs of the probe assembly and the tapered sensor housings facilitate the removal of the device from a tube hole without damage to the probe, cabling or spring mounts.

The apparatus of the invention has particular utility in the sensing and processing of eddy current signal response data to provide an estimation of the depths of cracks that initiate from the peripheral surface of header tube holes. An eddy current probe is preferably embodied within the one or more sensors 31, 32 of the probe assembly 30. The eddy current probe may be among one of several commercially available type probes and is operatively connected, via conventional electric lines 21, 23 or cable extending from the sensor housing, through the hollow cylinder 42.

The eddy current sensor 31, 32 is scanned along a circumferential path on the surface 14 of the hole 22. Eddy currents are induced in the electrically conducting header material by applying alternating currents to the eddy current coils. The probe is designed so that the components of the induced eddy currents are in a direction that is perpendicular to the plane of the crack. The well known skin effect associated with the eddy currently phenomenon concentrates the eddy currents near the surface of the header material. The induced currents tend to flow along the crack surfaces around the bottom and ends of the crack. This change in current path results in a corresponding change in the alternating magnetic field. The change in magnetic field in turn results in a change in the amplitude and phase of the voltage observed at the terminals of the coil. Commercially available eddy current instruments detect the change in amplitude and phase of the voltage to provide a signal response as the probe is scanned over a crack.

Eddy current signal responses caused by variables such as electrical conductivity, magnetic permeability and small variations in probe-to-material distance can be reduced or minimized by the incorporation of two coils. The coils can be positioned and oriented so that one coil exhibits a substantially different response to the crack than the other. For example, cross-wound coils can be designed and oriented so that one coil produces a minimum signal response to the crack while the other produces a maximum response. Since the coils are connected so that their respective signals subtract the signals caused by nondirectional variables such as electrical conductivity, magnetic permeability and probe-to-material distance will tend to cancel. Other differential coil configurations such as concentric coils and adjacent coils of various shapes and sizes can be used to achieve a similar reduction of these unwanted signal responses.

The eddy current probe can also be designed so that a relatively high frequency will provide greater resolution than that of a lower frequency. A multifrequency eddy current instrument can be used to obtain separate responses to two or more adjacent cracks. Appropriate signal responses have been obtained, for example, by using a cross-wound coil that is shielded with a thin brass foil approximately 0.005 inch thick. The brass foil contains a small hole at the position where coil windings cross. Relatively low frequencies, e.g. 1–10 KHz, penetrate through the foil. With this low frequency excitation, the coil provides a good response to increasing crack depth but can be influenced by two or more adjacent cracks at a given time. This multiple crack condition causes a signal response of greater width and amplitude than would occur for a single crack having identical dimensions. Relatively high frequencies, e.g., 500 KHz, produce a magnetic field that penetrates primarily through the small hole in the brass shield. This provides a high resolution indication and precise location of each of the cracks.

Low frequency response to multiple cracks is dependent on the number, spacing and lengths of the cracks as well as their respective depths. For example, two or more adjacent cracks can cause depth indications that are twice that of only one crack. The use of additional higher frequencies provides a basis for compensating for the errors in measuring crack depth when multiple cracks occur.

In accordance with a preferred technique for detecting and measuring cracks initiating from the surface 14 surrounding a header tube hole 22, the eddy current sensors, energized via the electrical lines 21, 23, to induce eddy currents in the surface to be inspected, are scanned in a circumferential direction by rotating the hollow cylinder 42. The scan may be repeated at additional axial locations by axially moving the hollow cylinder via operation of the drive rack 62. Signal responses are obtained at each location. In particular, two signal responses, such as the in-phase component and quadrature component or amplitude and phase is recorded for each frequency.

Various other features may be extracted from the signals and recorded in respect of the axial position of the scan.

The crack depth is then computed by using a formula that compensates for the errors caused by the proximity of two or more adjacent cracks of variable length and depth.

An example of a formula for estimating crack depth is given as follows:

$$D = C_{km}(A_{km})^2 - \sum_{i=1}^{N} (1/d_i)C_{ki}(A_{ki})^2 \Big|_{k=1}.$$

In general, the formula is a function of variables as indicated by:

$$D = F(A_{km}, A_{ki}, d_i, l_j)$$

where, $A_{km}$ = Maximum low-frequency signal component, k, acquired within a set of rotational scans $A_{ki}$ = Signal amplitude of one of the k components at circumferential location $X_i$ $X_i$ = Circumferential location of crack, i, determined from the high-frequency, high-resolution signal response $Z_{ij}$ = Axial location of the end j of crack i $d_i$ = Estimated lateral distance of crack at location $X_i$, from the position $X_m$, where the maximum occurs, i.e., $(X_m-X_i)$ $l_j$ = Estimated length of an adjacent crack at lateral position j, e.g., $(Z_{it}-Z_{ib})$ where t represents the top end of crack i and b represent the bottom end.

$C_{km}$ and $C_{ki}$ for i=1, 2, ... N are coefficients. The designation k=1 indicates that the amplitudes are acquired from the first component of the low frequency signal reponse.

In the case where there are no adjacent cracks, the formula reduces to the simple form:

$$D = C_m(A_{lm})^2$$

Similar formuli incorporating additional extracted features such as crack length and phase angle can be derived. Although the feature extraction and depth calculations can be determined by manual computation, microcomputer software can be designed to perform these computations with much greater efficiency and reliablity. The weighting coefficients, i.e., $C_{km}$ and $C_{kj}$, can be determined by using the least squared error criterion and guided random search techniques can be used to estimate coefficients when sufficient test sample data are available.

The technique generates and uses multifrequency eddy current signal response data to provide improved estimates of crack characteristics such as crack depth.

A microcomputer can be utilized to facilitate scan control, extraction of the numerical value of features and estimation of crack characteristics, e.g., depth and length. The preferred eddy current technique permits detection of cracks that may be missed by other inspection techniques such as penetrant and magnetic particle inspections. It does not require fluid coupling that may contaminate components and is relatively fast compared to other inspection methods and associated devices.

The invention claimed is:

1. An apparatus for scanning a peripheral surface encircling a portion of a header tube hole in a header while a tube stub having an inner diameter is seated within the hole, comprising:

a probe assembly capable of being inserted into the header tube hole having cantilevered spring means for resiliently urging at least one sensor mounted thereon into engagement with the peripheral surface to be scanned;

a tube stub mounting mechanism, capable of being inserted into the tube stub, having a central hollow cylinder connected to one end of the probe assembly, a flanged tube slidably disposed on the central hollow cylinder, a pair of expansible rings mounted on the flanged tube, and means mounted on the flanged tube for diametrically expanding the rings into engagement with the tube stub inner diameter to facilitate support and reference for the apparatus; and a drive carriage, attached to the tube stub mounting mechanism, having means for rotating the central hollow cylinder and the probe assembly connected to one end thereof so that the at least one sensor slides in the circumferential direction along the peripheral surface of the hole and means for axially translating the central hollow cylinder and the probe assembly connected to one end thereof so that the at least one sensor slides in the axial direction along the peripheral surface of the hole.

2. An apparatus, as recited in claim 1, wherein the probe assembly includes:

an elongated central support bar, and a clamp block, mounted on the elongated central support bar at a leading end of the probe assembly, for securing a first end of the cantilevered spring means to the elongated central support bar, the at least one sensor being connected proximate to a second end of the cantilevered spring means.

3. An apparatus, as recited in claim 2, wherein the elongated central support bar terminates beyond the second end of the cantilevered spring means in a C-shaped stop plate having stop lugs attached to a crossbar which overlap the second end of the cantilevered spring means to restrict lateral movement of the cantilevered spring means so that the probe assembly can be retrieved from the header without sustaining damage to the probe assembly and the at least one sensor.

4. An apparatus, as recited in claim 3, wherein the central hollow cylinder of the tube stub mounting mechanism is connected to the C-shaped stop plate of the probe assembly.

5. An apparatus, as recited in claim 4, wherein the at least one sensor has tapered edges to faciliate retrieval of the probe assembly from the header.

6. An apparatus, as recited in claim 1, where in the flange of the flanged tube lies on one side of one of the expansible rings, and where the means mounted on the flanged tube for diametrically expanding the rings into engagement with the tube stub inner diameter to facilitate support and reference for the apparatus comprises:
a rigid sleeve intermediate the expansible rings and an adjusting knob on one side of the other of the expansible rings, the adjusting knob being threadably engaged to the flanged tube for longitudinal movement on the flanged tube toward the expansible rings whereby the expansible rings are diametrically expanded responsive to pressure exerted by the rigid sleeve and the flange and by the rigid sleeve and the adjusting knob.

7. An apparatus, as recited in claim 1, wherein the at least one sensor comprises an eddy current probe.

8. An apparatus, as recited in claim 1, wherein the central hollow cylinder is flexible.

9. An apparatus, as recited in claim 8, wherein the flange of the flanged tube lies on one side of one of the expansible rings, and where the means mounted on the flanged tube for diametrically expanding the rings into engagement with the tube stub inner diameter,to facilitate support and reference for the apparatus comprises:
a first rigid sleeve intermediate the expansible rings; and a second rigid sleeve lying on one side of the other of the expansible rings, opposite the first rigid sleeve and lying intermediate the other of the expansible rings and an adjusting knob, the adjusting knob being threadably engaged to the flanged tube for longitudinal movement on the flanged tube towards the expansible rings, whereby the expansible rings are diametrically expanded responsive to pressure exerted by the first rigid sleeve and the flange and by the first rigid sleeve and the second rigid sleeve.

10. An apparatus, as recited in claim 1, wherein the cantilevered spring means comprises a pair of parallel, spaced spring bars, extending parallel to and on opposite sides of the elongated central support bar, and where one spring bar supports the at least one sensor while the other spring bar supports a housing fixture that does not contain a sensor, so that a counter force is provided to keep the probe assembly near the central axis of the header tube hole.

11. An apparatus, as recited in claim 10, wherein each of said pair of spring bars supports a sensor for scanning the peripheral surface of the hole.

12. An apparatus, as recited in claim 11, wherein the central hollow cylinder is made of type 304 stainless steel.

13. An apparatus, as recited in claim 1, wherein the expansible rings are comprised of rubber.

14. An apparatus, as recited in claim 1, wherein the means for rotating the central hollow cylinder and the probe assembly connected to one end thereof comprises:
a gear operatively attached to the central hollow cylinder for rotation via a bearing mounted on the drive carriage; and
means for imparting rotation to the gear operatively attached to the central hollow cylinder.

15. An apparatus, as recited in claim 14, wherein the means for imparting rotation to the gear operatively attached to the central hollow cylinder comprises an electronically controlled stepping motor attached to an intermediate gear for driving same.

16. An apparatus, as recited in claim 1, wherein the means for axially translating the central hollow cylinder and the probe assembly connected to one end thereof comprises:
a first and a second generally parallel mounting plates;
guide rods, disposed between the mounting plates and extending parallel to each other, which are slidably disposed on the second mounting plate so that the second mounting plate can advance or retract with respect to the first mounting plate;
a pinion gear, mounted on the first mounting plate, for driving a drive rack connected to the second mounting plate and which freely extends through the first mounting plate; and
means for imparting rotation to the pinion gear to rectilinearly advance or retract the second mounting plate with respect to the first mounting plate.

17. An apparatus, as recited in claim 16, wherein the means for imparting rotation to the pinion gear to rectilinearly advance or retract the second mounting plate with respect to the first mounting plate comprises a hand crank attached to the pinion gear.

18. An apparatus, as recited in claim 16, wherein the means for imparting rotation to the pinion gear to rectilinearly advance or retract the second mounting plate with respect to the first mounting plate comprises an electronically controlled stepping motor attached to the pinion gear.

19. A method for eddy current scanning a peripheral surface encircling a portion of a header tube hole in a header while a tube stub having an inner diameter is seated within the hole, comprising:
inserting into the portion of the header tube hole a probe assembly having cantilevered spring means for resiliently urging at least one eddy current probe mounted thereon into engagement with the peripheral surface to be scanned;
inserting into the tube stub a tube stub mounting mechanism, having a central hollow cylinder for axial and rotational movement and connected to one end of the probe assembly, a flanged tube slidably disposed on the central hollow cylinder, a pair of expansible rings mounted on the flanged tube, and means mounted on the flanged tube for diametrically expanding the rings into engagement with the tube stub inner diameter;
diametrically expanding the pair of expansible rings into engagement with the tube stub inner diameter so that the tube stub mounting mechanism is fixed in place while the central hollow cylinder, and the probe assembly attached to one end thereof, are supported and held in a fixed alignment with the portion of the header tube hole as the probe assembly is scanned over the peripheral surface;
moving the central hollow cylinder and, therewith, the probe assembly, relative to the peripheral surface being scanned; and
energizing the eddy current probe and detecting changes in the amplitude and phase of the voltage observed at the terminals of the eddy current probe as it is scanned over a defect.

* * * * *